(12) United States Patent
Warren et al.

(10) Patent No.: US 9,308,366 B2
(45) Date of Patent: Apr. 12, 2016

(54) REDUCTION AND REMOVAL OF PARTICLES DURING OR FOLLOWING SURGICAL PROCEDURES

(75) Inventors: Neil Warren, Penarth (GB); Robin Crossley, Windsor (GB); Steven Brown, Windsor (GB); Andrew Cheer, Cardiff (GB)

(73) Assignee: ASALUS MEDICAL INSTRUMENTS LIMITED, Cardiff (GB)

(*) Notice: Subject to any disclaimer, the term of this patent is extended or adjusted under 35 U.S.C. 154(b) by 718 days.

(21) Appl. No.: 13/291,728

(22) Filed: Nov. 8, 2011

(65) Prior Publication Data
US 2012/0067212 A1    Mar. 22, 2012

Related U.S. Application Data

(63) Continuation-in-part of application No. PCT/GB2010/051196, filed on Jul. 21, 2010.

(30) Foreign Application Priority Data

Jul. 23, 2009    (GB) .................................. 0912821.6

(51) Int. Cl.
*B03C 3/38*    (2006.01)
*A61N 1/20*    (2006.01)
(Continued)

(52) U.S. Cl.
CPC . *A61N 1/20* (2013.01); *A61B 18/00* (2013.01); *B03C 3/383* (2013.01); *B03C 3/41* (2013.01); *A61B 17/320068* (2013.01); *A61B 18/02* (2013.01); *A61B 18/1445* (2013.01);
(Continued)

(58) Field of Classification Search
CPC .................................. A61B 1/00; A61B 17/00
USPC ................................................................ 95/57
See application file for complete search history.

(56) References Cited

U.S. PATENT DOCUMENTS

| 4,057,064 A | 11/1977 | Morrison, Jr. et al. |
| 4,802,470 A | 2/1989 | Hara et al. |

(Continued)

FOREIGN PATENT DOCUMENTS

| CH | 618346 A5 | 7/1980 |
| CN | 2418951 Y | 2/2001 |

(Continued)

OTHER PUBLICATIONS

WO 2011/010148 A3 International Search Report Apr. 19, 2011 5 Pages.

(Continued)

*Primary Examiner* — Duane Smith
*Assistant Examiner* — Sonji Turner
(74) *Attorney, Agent, or Firm* — King & Schickli, PLLC

(57) ABSTRACT

Disclosed is apparatus 100 for the reduction or removal of smoke particles suspended in a local atmosphere A and resulting from a surgical procedure, the apparatus including or comprising two electrodes 140 and 150 each in electrical communication with or being electrically connectable to opposite poles of a source of high voltage dc electricity. A first of the electrodes 140 may be electrically connectable to a patient P. and a second 150 may be positionable within or adjacent a patient such that the two electrodes, when in communication with opposite poles of said high voltage, ionize said particles in use, for attracting said particles toward the patient or toward the second of the electrodes.

12 Claims, 6 Drawing Sheets

(51) Int. Cl.
   *A61B 18/00* (2006.01)
   *B03C 3/41* (2006.01)
   *A61B 17/32* (2006.01)
   *A61B 18/02* (2006.01)
   *A61B 18/14* (2006.01)
   *A61B 18/20* (2006.01)

(52) U.S. Cl.
   CPC ...... *A61B 18/20* (2013.01); *A61B 2018/00083* (2013.01); *A61B 2018/00601* (2013.01); *A61B 2018/1497* (2013.01); *A61B 2218/008* (2013.01); *B03C 2201/10* (2013.01); *B03C 2201/26* (2013.01)

(56) References Cited

U.S. PATENT DOCUMENTS

| | | | |
|---|---|---|---|
| 4,854,500 A | | 8/1989 | Mathai et al. |
| 4,901,719 A | * | 2/1990 | Trenconsky et al. ............ 606/49 |
| 4,911,737 A | | 3/1990 | Yehl et al. |
| 5,218,973 A | * | 6/1993 | Weaver et al. ................ 607/152 |
| 6,379,427 B1 | | 4/2002 | Siess |
| 6,513,529 B1 | | 2/2003 | Kamen |
| 7,041,096 B2 | * | 5/2006 | Malis et al. ..................... 606/34 |
| 7,300,436 B2 | * | 11/2007 | Penny et al. .................... 606/34 |
| 2003/0147784 A1 | * | 8/2003 | Joannou ................... 422/186.04 |
| 2007/0000501 A1 | | 1/2007 | Wert et al. |
| 2010/0089234 A1 | * | 4/2010 | Khoury .............................. 95/81 |

FOREIGN PATENT DOCUMENTS

| | | |
|---|---|---|
| DE | 8809124 U1 | 2/1989 |
| DE | 3824351 A1 | 1/1990 |
| DE | 3915907 A1 | 6/1990 |
| DE | 202006009481 U1 | 10/2006 |
| GB | 2406793 A | 4/2005 |
| JP | S62149359 A | 7/1987 |
| JP | 2001108269 A | 4/2001 |
| WO | 9915091 A1 | 4/1999 |

OTHER PUBLICATIONS

GB0912821.6 Search Report Nov. 17, 2009 4 Pages.

* cited by examiner

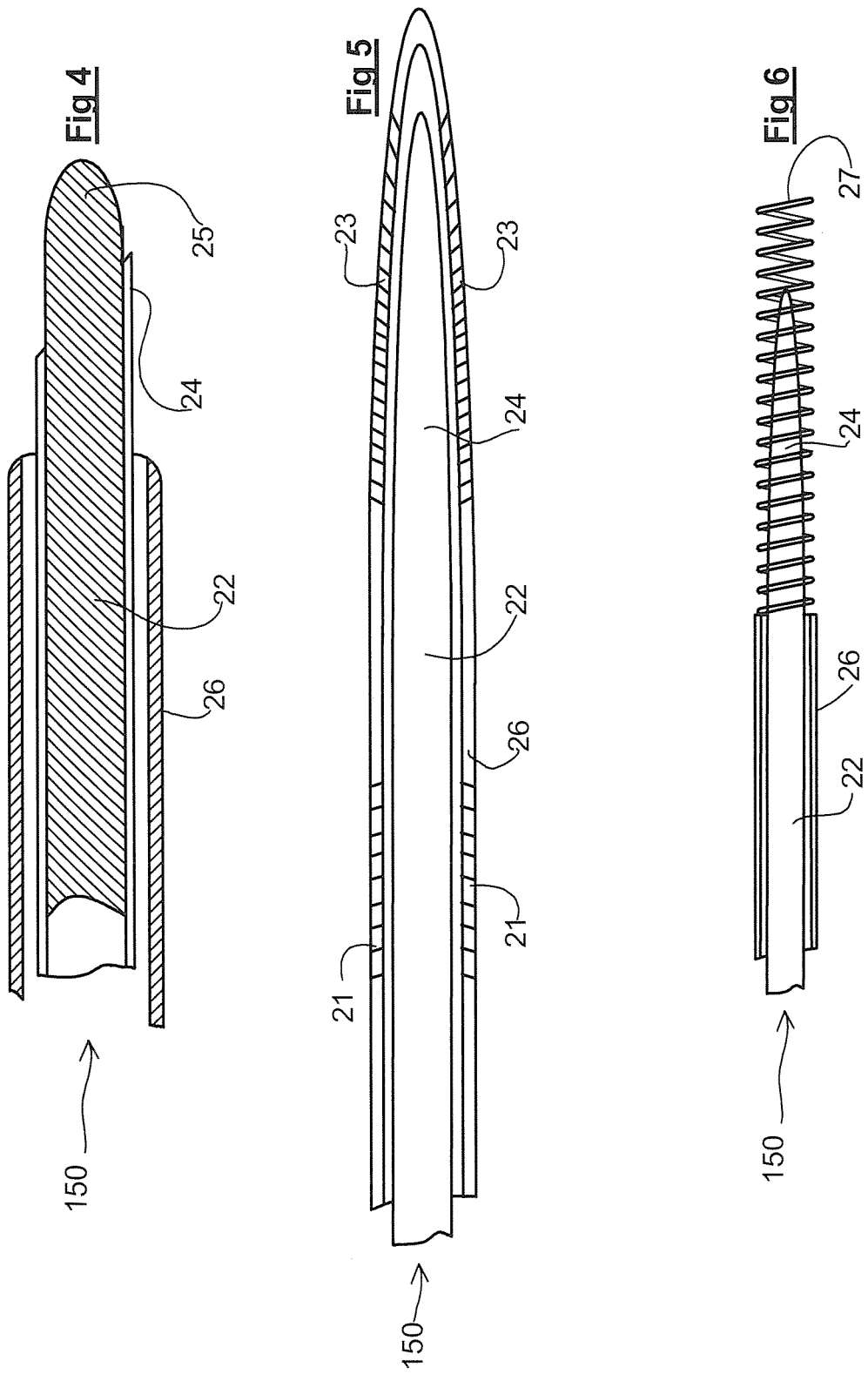

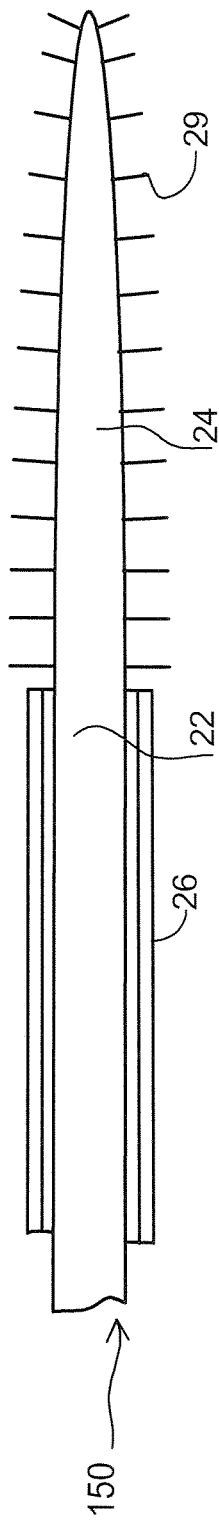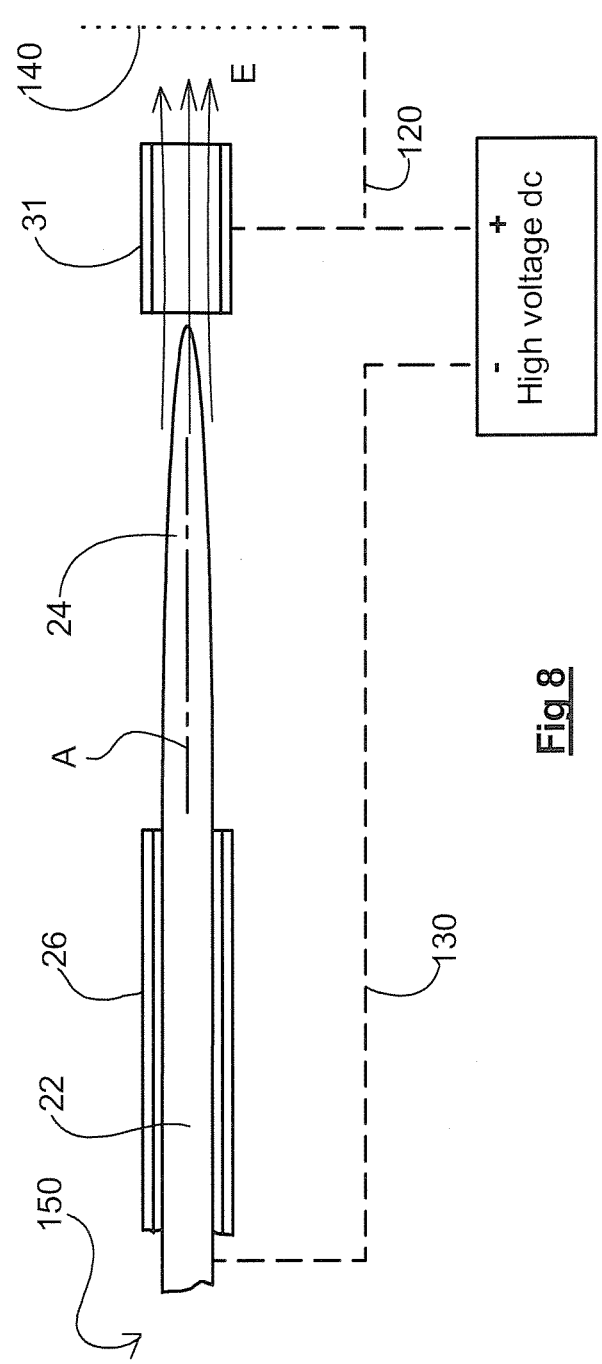

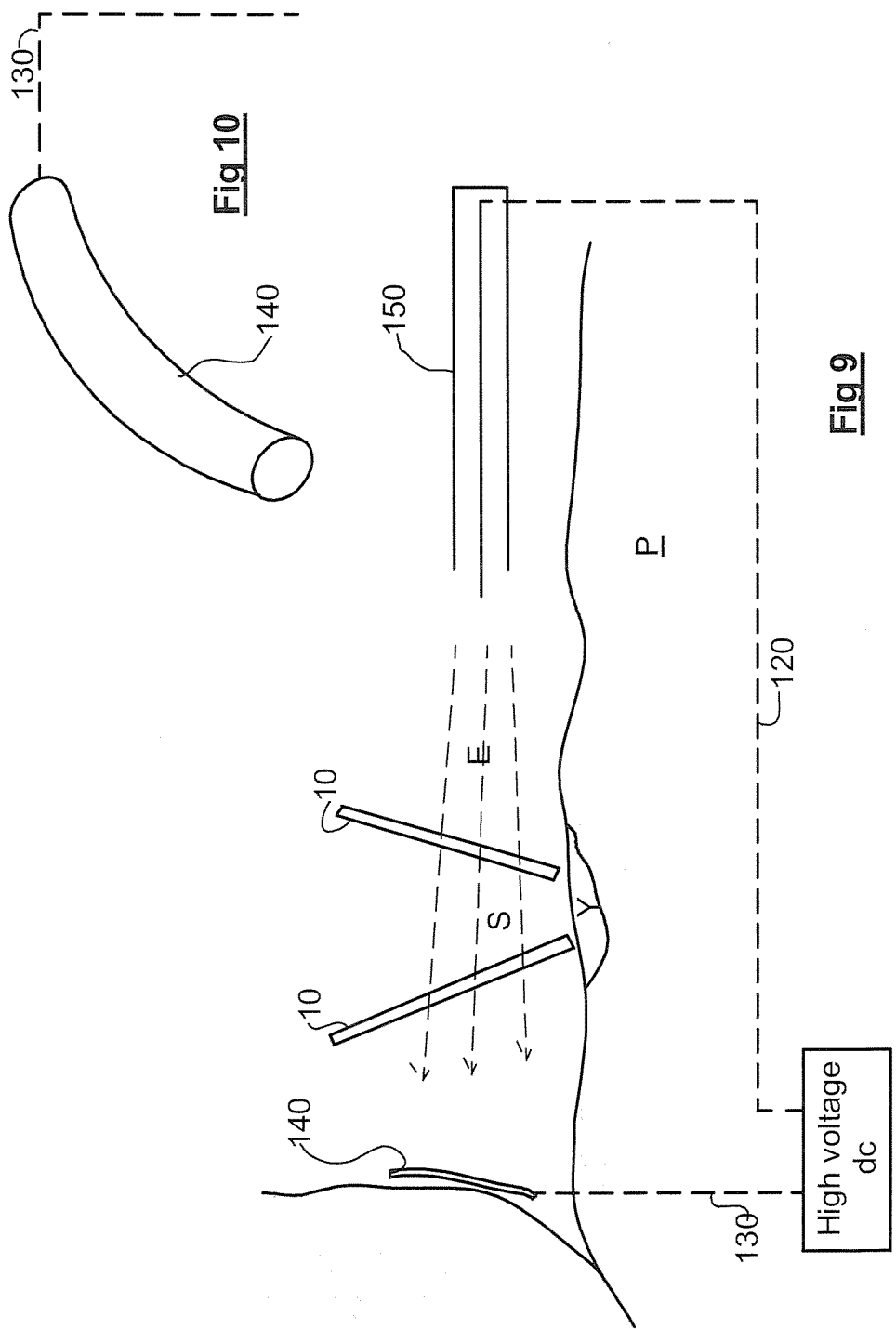

REDUCTION AND REMOVAL OF PARTICLES DURING OR FOLLOWING SURGICAL PROCEDURES

This application is a continuation-in-part of PCT/GB2010/051196, filed Jul. 21, 2010, which claims priority from British Patent Application Ser. No. 0912821.6, filed Jul. 23, 2009, the disclosures of which are incorporated herein by reference.

FIELD OF THE INVENTION

This invention relates to the reduction or removal of particles, during or following surgical procedures, in particular, but not exclusively, the reduction or removal of smoke during or following procedures such as laparoscopic or other intracorporeal procedures or open surgery.

In this specification the words particles, smoke, smoke particles, and related terms are intended to encompass any particles, or molecules or matter suspended in an atmosphere including suspended droplets formed by heat or cold.

BACKGROUND OF THE INVENTION

Particles such as smoke particles are often generated during surgical procedures. Heat can be generated, for example when electrical current is passed through tissue for cutting, when friction cutting is employed, where intense light such as light generated by lasers is used, or any technique which uses large amounts of energy.

Smoke particles generated in this way obscure the view of a surgeon when operating and may be hazardous. Development of smoke removal methods when conventional surgery is used has concentrated on removing the smoke by means of a vacuum and then either venting the smoke externally of the operating theatre and/or filtering out the smoke particles. When laparoscopic procedures are carried out, gas is introduced into the patient via access ports to inflate the area of the patient's body that is of interest. Smoke generated in the insufflated area, for example when diathermic or electrocautery cutting is undertaken, is sucked out and may then be filtered. The smoke particles should be filtered out but often, in practice, they are not. Filters for such vacuum smoke removal are expensive. Often the smoke is left to permeate into the operating theatre in many procedures.

Even when cryosurgery is employed, frozen vapour, droplets, or matter can be generated like fog, which is suspended in the local atmosphere. This fog too is intended to be encompassed by the term 'particles' in this specification. The fog too can obscure the surgeon's view.

The inventor has realised that a different approach to suspended particle reduction or removal is required and embodiments of the invention address the problems mentioned above.

SUMMARY OF THE INVENTION

According to a first aspect the invention comprises apparatus for the reduction or removal of particles suspended in a local atmosphere and resulting from a surgical procedure, the apparatus including or comprising two electrodes each in electrical communication with or being electrically connectable to opposite poles of a source of high voltage dc electricity, a first of the electrodes being electrically connectable to a patient, and a second being positionable within or adjacent a patient such that the two electrodes, when in communication with opposite poles of said high voltage, ionise said particles in use, for attracting said particles toward the first electrode or second electrode, depending on polarity.

In an embodiment the apparatus is arranged to attract the particles toward the first electrode and hence toward the main body of the patient when said first electrode is connected to the patient.

Alternatively the apparatus is arranged to attract the particles toward the second electrode and hence towards the skin of the patient.

In an embodiment, the first electrode includes or comprises at least one conductive pad for direct or indirect contact with a patient's skin.

In an embodiment the second electrode includes or comprises at least one electrically conductive element which may be mounted or mountable to a surgical instrument or tool.

In an embodiment, the second electrode forms part of a surgical instrument which is capable of generating said particles in use.

Preferably the second electrode includes an electrically insulative shield for preventing electrical contact between the second electrode and the patient.

Preferably the shield has a cavity and an opening in the cavity, and the cavity is pressurised for causing a flow of gas out of the opening. This helps to keep the second electrode substantially clear of foreign matter.

Alternatively, or as well as, the pressurised shield for the second electrode may include a wiper. The wiper aids removal of foreign matter at the second electrode.

In an embodiment, the high voltage is an electrical supply within a range of about 1 kV to about 30 kV, and preferably around 5 kV to 10 kV.

In an embodiment, the voltage source includes a current regulator. It is envisaged that the current regulator will limit the amount of current flowing across the high voltage source to less than 10 µA, for example around 1 to 5 µA.

According to a second aspect the invention comprises a method of reducing or removing particles suspended in a local atmosphere, during and/or after surgical procedures, the method comprising the steps in any suitable order, of:
  a) providing a source of high voltage dc electricity;
  b) electrically connecting a patient to one pole of said source;
  c) electrically connecting a conductive element to the other of the poles of said source
  d) positioning said element in the atmosphere to thereby ionise said particles and attract said particles toward the patient or toward the element, depending on polarity.

In an embodiment, in the method step b) said one pole is the positive pole, in step c) the other of the poles is the negative pole and in step d) the particles are attracted toward the patient when electrons are emitted by the instrument.

According to a third aspect the invention provides a method of reducing or removing particles suspended in a local atmosphere, during and/or after surgical procedures, the method comprising the steps in any suitable order, of:
  a) providing a source of high voltage dc electricity;
  b) electrically connecting one pole of said source to a first electrode;
  c) electrically connecting a conductive element having an axis, to the other of the poles of said source;
  d) positioning said element in the atmosphere with its axis directed to the first electrode, to thereby ionise said particles and attract said particles toward the first electrode.

In an embodiment, in the method step b) said one pole is the positive pole, in step c) the other of the poles is the negative pole and in step d) the particles are attracted toward the first electrode when electrons are emitted by the element.

The invention extends to any novel feature described or illustrated herein, or any combination of features which is novel, and is described or illustrated herein.

BRIEF DESCRIPTION OF THE DRAWING FIGURES

The invention can be put into effect in numerous ways, examples only being described below, with reference to the drawings, wherein:

FIGS. 4, 5, 6, 7 and 8 show different embodiments of an electrode; and

FIGS. 9 and 10 show further applications of the invention.

DETAILED DESCRIPTION OF THE INVENTION

Figure 1:
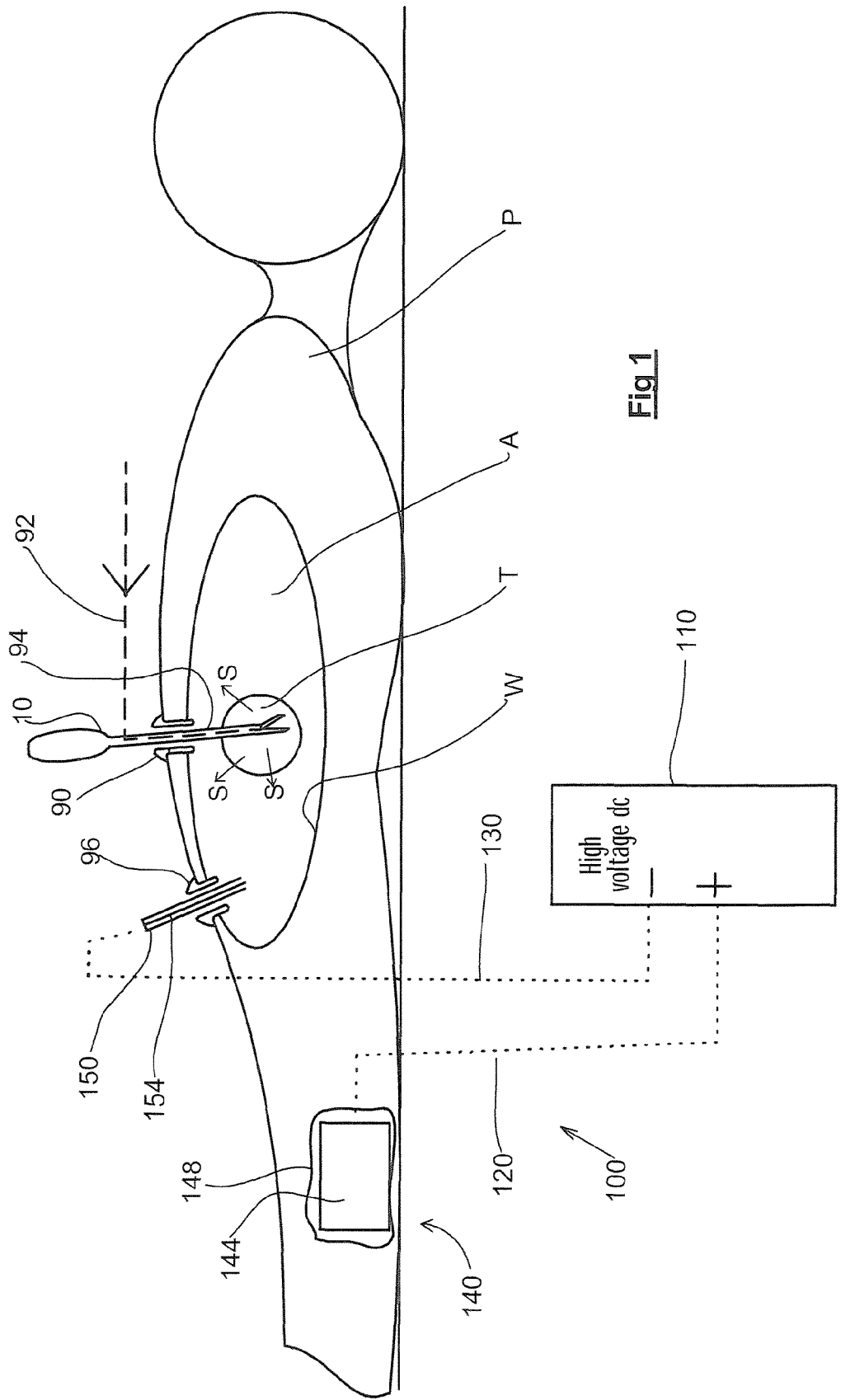
FIG. 1 shows a first arrangement for the removal or reduction of smoke particles from the abdomen of a patient.

Referring to FIG. 1 there is shown a patient P who is undergoing a laparoscopic procedure. An instrument 10, is inserted into the insufflated abdomen A via a laparoscopic access port 90 and is being used to for removal of tissue T in the abdomen A of the patient P. The instrument 10 is supplied with power along a power supply route 92. The instrument 10 is producing smoke particles S. It should be noted that the term smoke particles in this description includes particles, vapour, and other matter which is mixed or suspended in the atmosphere within the abdomen A. The above mentioned features are conventional.

Apparatus 100 is provided to reduce or remove the smoke S from the abdomen A. The apparatus includes a high voltage dc electrical source 110, insulated conductors 120 and 130, a first electrode 140 in the form of a conductive pad 144, and a second electrode 150. An example of the construction of the second electrode is given below, although in its simplest form the second electrode is a conductive rod 154 which is partially insulated to prevent the rod from being touched accidentally against the patient P.

In use the conductive pad 144 of the first electrode is attached to the leg of the patient P, or other body part, using a conductive gel 148 and electrically connected to the positive pole of the high voltage source by means of insulated conductor 120. The patient's body then becomes positively charged.

The second electrode 150 is connected to the negative pole of the high voltage source 110 via insulated conductor 130. The second electrode may be inserted into the abdomen A through a bespoke introducing device 96 shown generally in FIG. 1 or through a conventional plastic laparoscopic access port 90.

The second electrode is negatively charged and, in keeping with accepted theory, sends a stream of electrons toward the wall W of the patient's body. Further, in keeping with accepted theory, the electrons attach themselves to some of the atoms of the smoke particles causing the atoms to form negative ions and to thereby become attracted to the positively charged walls of the abdomen. Thus, the smoke particles S are attracted toward the positively charged walls W of the abdomen A, where they stick and are then washed away at the end of the surgical procedure.

Figure 2:
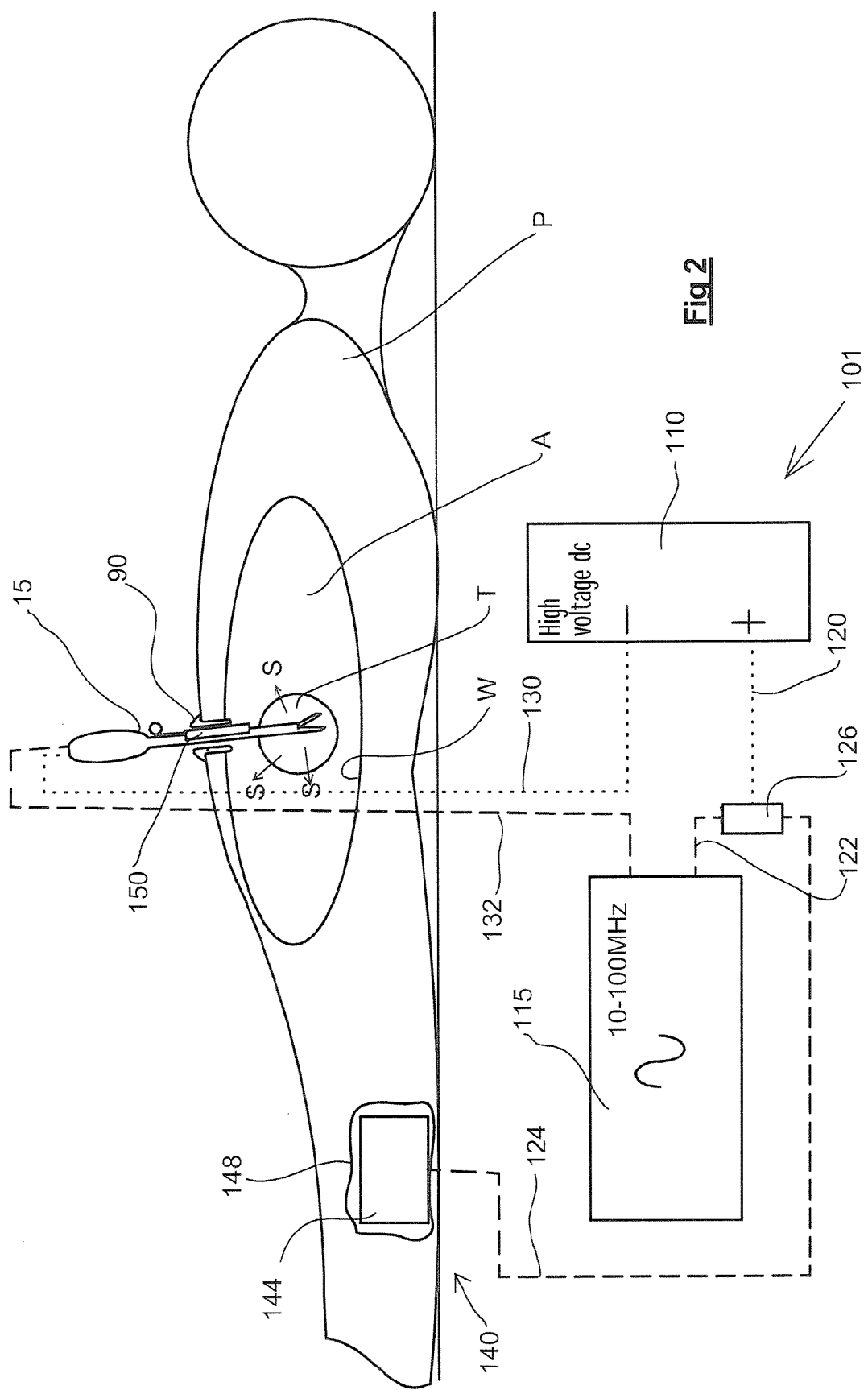
FIG. 2 shows a second arrangement for the removal or reduction of smoke particles from the abdomen of a patient.

FIG. 2 shows an arrangement 101 which is similar to the arrangement 100 described above, where like parts have like reference numerals, and where the same ionising principle of operation is employed. However, in this second arrangement, the second electrode 150 is incorporated with a surgical cutting instrument 15.

Instrument 15 is a modified electrosurgical device, also known as a diathermy device, which uses a high frequency electrical current source 115 having a frequency of between 100 KHz and 100 MHz, passed through the patient to produce heat at the tip of the instrument, for cutting and cauterisation at a cutting area. The ac current is passed along conductors 122 and 132 to, respectively, the pad 144 and the instrument 15. When the surgeon switches on the current and touches the patient, then cutting of tissue T is performed because the current circuit is completed and the local impedance of the tissue results in heat being generated. It will be noted that the conductors 122 and 120 share the same path 124 in this instance and that the conductor 120 is connected to conductor 122 by a connecting piece 126.

The second electrode 150 is mounted to the instrument 15 and is supplied with dc high voltage by the insulated conductor 130.

Figure 3:
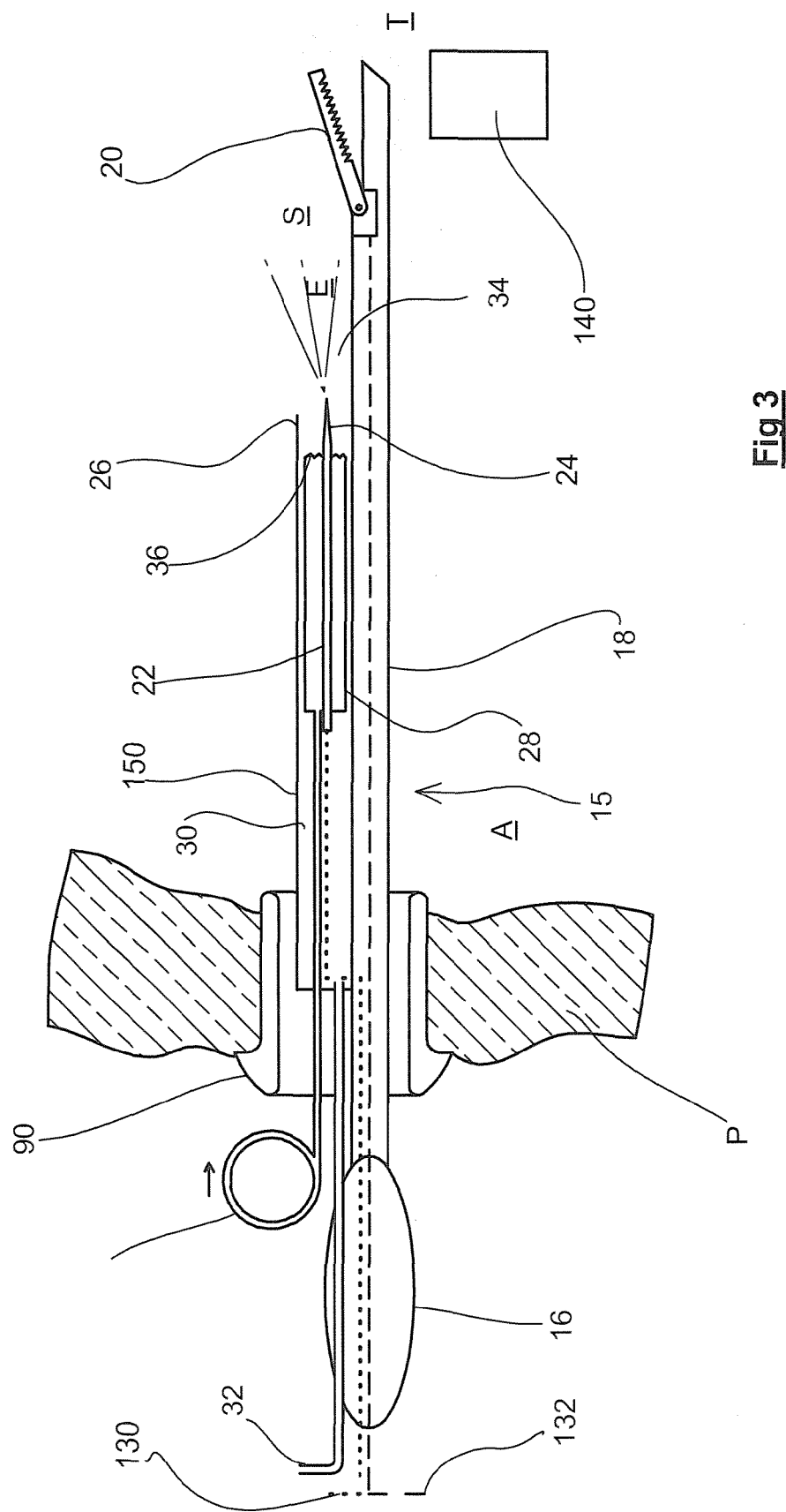
FIG. 3 shows an arrangement of an electrode for use in the second arrangement.

FIG. 3 shows a larger scale view of the electrosurgical instrument 15, shown in section. The instrument includes a handle 16, a body portion 18, a cutting head 20 and the conductor 132 fitted centrally of the body 18. In use the surgeon inserts the instrument into an access port 90. When the current is supplied and the cutting head 20 is engaged with tissue T, excision of the tissue can be performed. This procedure produces smoke S which can be removed or reduced by ionisation as described above.

Electrode 150 is fitted to the body 18 of the instrument 15. The electrode 150 includes a conductive rod 22 having a pointed tip 24, and a shield 26 which prevents direct contact between the tip 24 and the patient P. The electrode further includes a housing 28 having a cavity 30 which can be pressurised via a gas supply route 32. The pressurised gas can escape at the opening 34 of the housing 28. This gas flow helps to prevent foreign matter entering the opening 34. In addition, a wiper 36 can be advanced by means of a pusher 38, from inside the housing 28 toward the opening 34 to dislodge any foreign matter that enters the opening 34.

When it is desired to remove smoke from the abdomen A, the high voltage dc supply can be switched on and a stream of electrons E are generated. As described above the effect of the electrons is to ionise any particles or matter suspended in the local atmosphere to cause the ionised particles etc to be attracted to the positively charged patient as mentioned above. The ionisation can be during or after the electrosurgical procedure.

FIGS. 4 to 8 each show modified tip portions of the second electrode 150. In FIG. 4 the electrode 150 is in the form of a hollow cannula with a sharp tip 24, with an electrically insulating shield 26. A non-conductive rod 22 extends through the lumen of the hollow electrode 150 and extends beyond the tip 24. The rounded tip 25 of rod 22 serves to minimise any risk of unintentional damage to the patient caused by the sharp tip 24. In use, a small incision in the patient P can be made and used to introduce the electrically insulating shield 26 percutaneously. The electrode 150 can then be inserted through the lumen of the insulating shield 26.

FIG. 5 shows a tip portion of a further electrode 150 including a pointed tip 24 covered by an electrically insulating shield 26. In this case, the shield has a series of inlet apertures 21 and outlet apertures 23 providing, respectively, an inlet and an outlet for charged air molecules to flow. Apertures 21 and 23 are for illustrative purposes only and may be of different sizes and configurations to maximise the performance and safety of the device in use.

FIG. 6 shows a further electrode 150, including conductive rod 22 having a tip 24 and a shield 26. The shield terminates in a coiled spring-like formation 27 which covers the tip 24 and protects the patient from unintended trauma caused by tip 24 when in use. In one version the spring 27 is not conductive and acts solely as a shield for said protection which can retract on insertion to expose the tip 24, whereas in another version the spring 27 may be conductive to improve the performance of the electrode in producing electrons, but need not be retractable to expose the tip 24. In this latter configuration it is the coiled formation that releases the electrons to form ions.

FIG. 7 shows a further electrode 150 including a shield 26 and a tip 24, as well as a plurality of fine hair-like conductive elements, such as stainless steel fibres to provide an improved surface for shedding electrons and thus generating ions. The fibres 29 are resilient to allow insertion of the tip 24 into the patient via insertion into the lumen of the shield 26. Shield 26 may be wide enough to accommodate the entire width of the electrode, or alternatively the fibres may be compressed during insertion but spring back into position when extending beyond the end of shield 26.

FIG. 8 shows a further electrode embodiment, incorporating a positively charged accelerator ring 31. The accelerator ring 31 improves the performance of the electrode 150, by drawing ions in the direction of their intended flow, in this case towards the second electrode 140.

FIG. 9 shows an arrangement for reducing or removing particles, for example smoke particles from an extracorporeal surgical site Y. In this case, an electrode 140 is placed generally in the axis A of the electrode 150, for best results. In this orientation, a stream of electrons E which generates ions is directed over the surgical site Y to coincide with smoke particles S generated by surgical tools 10 at the site Y. In this embodiment the electrode 140 will attract the particles to its surface. The electrode 140 can take various forms, for example, a nickel gauze which can be washed after use, a mat of conductive material, for example random plastic fibres coated in a conductive carbon slurry, or a metallic plate. In any event, it will be apparent that the patient is not used as a conductive path and therefore the smoke particles are attracted directly to the electrode. After use the electrode 140 can be washed and sterilised for reuse, or disposed of, as a consumable item.

FIG. 10 shows an alternative electrode 140 in the form of a flexible cylinder supply by path 130. The cylinder can be inserted into a patient, for example through a surgical access port 90. It is intended that the smoke particles be attracted directly to the electrode 140 shown in FIG. 10, and so when the electrode is removed it can be disposed of or cleaned, so that the smoke particles which were attracted to the electrode are removed from the body cavity of the patient following the surgical procedure.

It will be apparent to the skilled addressee that many modifications, variants and improvements are possible within the ambit of the invention defined herein. For example, the first two arrangements shown are intracorporeal, however a similar method can be employed during the extracorporeal procedure shown in FIG. 9. In FIGS. 1 and 2, the patient has been positively charged so that the ionised particles etc are attracted to the patient. If the polarity in those arrangements shown was reversed then the particles etc will be attracted to the electrode 150, and, for example can be wiped off the electrode when necessary using wiper 36 or a similar device.

Although a dc voltage of up to 30 kV could be used, lower voltages will be sufficient. For example around 8 or 9 kV voltage is envisaged, with a current limiting regulator in the form of a series resistor maintaining the current at a safe limit for the patient and operator. A clean reasonably constant voltage is preferred, but a voltage which is fluctuating could be used, particularly where the apparatus is employed in conjunction with an electrically driven surgical tool, provided there is no current reversal. In this description 'dc' is intended to cover an oscillating or a noisy voltage which is biased to provide current only in one direction in a circuit. Ionising radiation is, in the arrangements described above, generated using electrical potential difference, although other forms of radiation may be used such as radiation from radio active substances. Attraction of the ionised particles to the patient could then achieved by earthing the patient.

The invention may be incorporated into any monopolar electrosurgical device by means of arranging the particle removal apparatus as shown in FIG. 2, or where a bipolar electrosurgical device is employed, which does not use a patient return (first) electrode i.e. does not require a current path through the patient, or any other particle generating device, the arrangement shown in FIG. 1 can be employed. In addition, devices which do not use electrical energy for cutting etc could be used and their resultant particle production can be removed or reduced by employing the apparatus described above, for example laser devices, or ultrasound-powered cutting tools that cut and seal tissue simultaneously (harmonic scalpels) could be used. Cryosurgical devices could be used also. Further, one of the electrodes could be incorporated into the access port 90 shown in FIG. 1 or a similar port.

A mains power supply is intended to be used for the generation of the high voltage, but may be replaced or supplemented by a rechargeable storage battery. The mains/battery power supply, or the conductor 130 may be constant or interrupted by a switch operable by a surgeon or his/her assistant, for example a thumb operated switch or a foot pedal, to provide manual control.

In order to improve safety it is envisaged that a control means will be provided to monitor the current travelling in the high voltage circuit, which will stop the flow of current very quickly should the current increase rapidly in a short space of time, i.e. should a short circuit be detected, for example where the second electrode touches the body of the patient. This will avoid or reduce accidental voltage shocks to the patient. In addition it is possible to monitor increased impedance, and thereby detect a blocked electron emission. It has been found that the apparatus works best for particle removal or reduction, when the axis of the conductive part of the second electrode 150, e.g. the conductive element 22, is directed toward the first electrode 140. This can usually be achieved in abdominal laparoscopic procedures, by placing the first electrode adjacent the surgical site on a patient. Also it has been found that performance is improved when the tip of the second electrode is exposed by at least 5 mm or is open to the surgical atmosphere. Optionally the electrodes are disposable.

The invention claimed is:

1. Apparatus for the reduction and removal of particles suspended in a local atmosphere and resulting from a surgical procedure at a site on a patient having a body, the apparatus including or comprising two electrodes, each in electrical communication with or being electrically connectable to opposite poles of a source of high voltage DC electricity, the first electrode being connectable to the body of the patient undergoing the surgical procedure and the second electrode comprising a conductive rod extending through an insulating elongated shield, the rod having an exposed distal end, the rod and the second electrode being adapted to be removably inserted at or near the site of the surgical procedure such that, in use, the two electrodes, when in communication with opposite poles of said high voltage DC electricity, ionise said suspended particles, for attracting said suspended particles towards the patient.

2. Apparatus as claimed in claim 1, wherein the first electrode includes or comprises at least one conductive pad for direct or indirect contact with a patient's skin.

3. Apparatus as claimed in claim 1, wherein the second electrode includes or comprises at least one electrically conductive element which forms part of or is mounted or mountable to a surgical instrument or tool.

4. Apparatus as claimed in claim 3, wherein the surgical instrument or tool is capable of generating said suspended particles generated by the surgical procedure of the patient.

5. Apparatus as claimed in claim 1, wherein said shield has apertures to allow entry and egress of air into and out of the shield.

6. Apparatus as claimed in claim 1, wherein the second electrode includes an oppositely charged accelerator located beyond the tip of the electrode.

7. Apparatus as claimed in claim 1, wherein the shield has a cavity and an opening in the cavity, and the cavity is pressurised for causing a flow of gas out of the opening.

8. Apparatus as claimed in claim 1, wherein the second electrode includes a wiper for removal of foreign matter at the second electrode.

9. Apparatus as claimed in claim 1, wherein the high voltage is an electrical supply within a range of about 1 kV to about 30 kV, and preferably around 5 kV to 10 kV.

10. Apparatus as claimed in claim 1, wherein the voltage source includes a current regulator, preferably limiting the amount of current flowing across the high voltage source to less than 10 $\mu$A.

11. A method of reducing or removing particles suspended in a local atmosphere, during and/or after a surgical procedure, the method comprising the steps in any suitable order, of:
   a) providing a source of high voltage DC electricity;
   b) electrically connecting the body of a patient undergoing the procedure to one pole of said source using a first electrode;
   c) electrically connecting a second electrode comprising a conductive rod, which extends through an insulating elongated shield and which comprises an exposed distal end, to the other of the poles of said source;
   d) inserting said second electrode in the atmosphere to thereby ionise said suspended particles and attract said particles toward the patient.

12. In connection with an apparatus for the reduction and removal of particles suspended in a local atmosphere and resulting from a surgical procedure at a site on a body of a patient, the improvement comprising two electrodes, each in electrical communication with or being electrically connectable to opposite poles of a source of high voltage DC electricity, the first electrode being connectable to the body of the patient undergoing the surgical procedure and the second electrode comprising a conductive rod extending through an insulating elongated shield, the rod having an exposed distal end, the rod and the second electrode being adapted to be removably inserted at or near the site of the surgical procedure such that, in use, the two electrodes, when in communication with the opposite poles of said high voltage DC electricity, ionise said suspended particles for attracting said suspended particles towards the patient.

* * * * *